United States Patent [19]

Jung

[11] Patent Number: 5,200,404
[45] Date of Patent: Apr. 6, 1993

[54] 3-TETRAZOLYLTHIOMETHYL CEPHALOSPORIN ANTIBIOTICS

[75] Inventor: Frederick H. Jung, Taissy, France

[73] Assignee: ICI Pharma, Cergy Cedex, France

[21] Appl. No.: 670,863

[22] Filed: Mar. 18, 1991

[30] Foreign Application Priority Data

Mar. 16, 1990 [EP] European Pat. Off. ........ 90400724.2

[51] Int. Cl.$^5$ ................. C07D 501/36; A61K 31/545
[52] U.S. Cl. ...................................... 514/206; 540/227
[58] Field of Search ................. 540/226, 227, 222; 514/206

[56] References Cited

U.S. PATENT DOCUMENTS

| | | | |
|---|---|---|---|
| 3,926,957 | 12/1975 | Gregson et al. | 260/239.1 |
| 3,991,046 | 11/1976 | Gregson et al. | 260/239.1 |
| 4,024,134 | 5/1977 | Gregson et al. | 260/243 C |
| 4,399,131 | 8/1983 | Durckheimer et al. | 424/246 |
| 4,493,833 | 1/1985 | Takaga et al. | 540/222 |
| 5,057,511 | 10/1991 | Jung et al. | 540/227 |

FOREIGN PATENT DOCUMENTS

| | | |
|---|---|---|
| 0013762 | 8/1980 | European Pat. Off. |
| 0272827 | 6/1988 | European Pat. Off. |

OTHER PUBLICATIONS

Chemical Abstracts, vol. 109, No. 7, pp. 658–659, Aug. 15, 1988.

*Primary Examiner*—Nicholas S. Rizzo
*Attorney, Agent, or Firm*—Cushman, Darby & Cushman

[57] ABSTRACT

A compound of the formula (II):

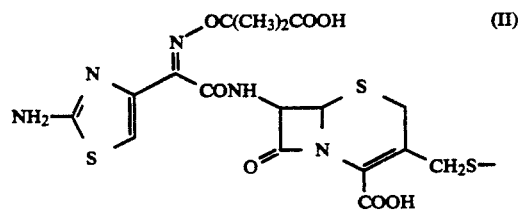

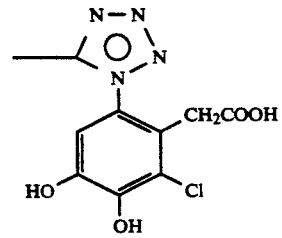

and pharmaceutically acceptable salts an in vivo hydrolysable esters are described as is their preparation and use as antibacterial agents.

8 Claims, No Drawings

3-TETRAZOLYLTHIOMETHYL CEPHALOSPORIN ANTIBIOTICS

The present invention relates to cephalosporin compounds and in particular to (3-chloro-4,5-dihydroxyphenyl)tetrazol-5-yl thiomethyl cephalosporins having a particularly desirable profile of activity and duration in antibacterial effect. This invention further relates to processes for their preparation, to intermediates in their preparation, to their use as therapeutic agents and to pharmaceutical compositions containing them. The compounds of this invention are antibiotics and can be used in the treatment of any disease that is conventionally treated with antibiotics, for example in the treatment of bacterial infection in mammals including humans.

Our own European Patent Application 272827 discloses cephalosporin compounds having a 3-position substituent of the formula (I):

wherein

Q represents a 5- or 6- membered heterocyclic ring containing 1–4 heteroatoms selected from oxygen, nitrogen and sulphur (optionally fused to a benzene ring or to a further such heterocyclic ring) wherein Q optionally, where possible, may bear a positive charge and may optionally be substituted on an available carbon or nitrogen atom by carboxy, sulpho, $C_{1-4}$alkoxycarbonyl or $C_{1-4}$alkyl (which alkyl group may itself optionally be substituted by carboxy, or $C_{1-4}$alkoxycarbonyl);

P represents:

(i) a benzene ring (optionally fused to a further benzene ring (so forming a naphthyl group) or to a 5 or 6 membered heterocyclic aromatic group containing 1, 2 or 3 heteroatoms selected from nitrogen, oxygen and sulphur) said benzene ring (or in the case of naphthyl either benzene ring) substituted by groups $R^1$ and $R^2$ which are ortho with respect to one another wherein $R^1$ is hydroxy or an in vivo hydrolysable ester thereof and $R^2$ is hydroxy, an in vivo hydrolysable ester thereof, carboxy, sulpho, hydroxymethyl, or ureido;

(ii) a group of the formula:

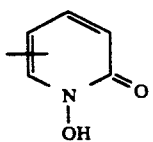

or;

(iii) a group of the formula:

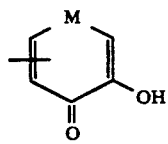

wherein M is oxygen or a group $NR^3$ wherein $R^3$ is hydrogen or $C_{1-4}$ alkyl:

ring P (or, in the case wherein ring P is a benzene ring and is fused to another benzene ring, either benzene ring) is optionally further substituted by $C_{1-4}$ alkyl, halo, hydroxy, hydroxy $C_{1-4}$ alkyl, cyano, trifluoromethyl, nitro, amino, $C_{1-4}$ alkylamino, di- $C_{1-4}$ alkylamino, amino $C_{1-4}$ alkyl, $C_{1-4}$ alkylamino $C_{1-4}$ alkyl, di-$C_{1-4}$ alkylamino $C_{1-4}$ alkyl, $C_{1-4}$ alkanoyl, $C_{1-4}$ alkoxy, $C_{1-4}$ alkylthio, $C_{1-4}$ alkanoyloxy, carbamoyl, $C_{1-4}$ alkylcarbamoyl, di-$C_{1-4}$ alkyl carbamoyl, carboxy, carboxy $C_{1-4}$ alkyl, sulpho, sulpho $C_{1-4}$ alkyl, $C_{1-4}$ alkanesulphonamido, $C_{1-4}$ alkoxycarbonyl, $C_{1-4}$ alkanoylamino, nitroso, thioureido, amidino, ammonium, mono-, di- or tri- $C_{1-4}$ alkylammonium pyridinium, or a 5-membered heterocyclic ring containing 1 to 4 heteroatoms selected from oxygen, nitrogen and sulphur which is optionally substituted by 1, 2 or 3 $C_{1-4}$ alkyl or $C_{1-4}$ alkoxy groups, n=0 or 1 such that when n=1 Y represents a covalent bond between Q and P or a $C_{1-4}$alkylene group optionally substituted by carboxy or sulpho or Y represents a group —(CH$_2$)$_m$—Y'—wherein m=1 or 2 and Y' is —O.CO— or —NH.CO—; and when n=0 Q and P both represent monocyclic rings which are fused on an available carbon-carbon or carbon-nitrogen bond.

Various 7-position substituents for such compounds are also disclosed.

Investigation into new cephalosporin derivatives has been intense over the past 25 years with many thousands of patents and scientific papers having been published. A particular problem associated with most of the commercially available cephalosporins is the lack of potency against strains of Pseudomonas.

A further problem associated with many commercially available cephalosporins is the lack of stability to beta-lactamase-producing organisms and the consequent reduction of antibacterial activity.

We have now discovered a combination of substituents that provides a cephalosporin having particularly desirable activity and duration.

The compound of the present invention possesses very good antibacterial activity and in particular against strains of *Pseudomonas aeruginosa*. In addition, the compound of the present invention exhibits good stability, in general, to beta-lactamases and is particularly useful in inhibiting organisms that are beta-lactamase producers. These organisms are of increasing concern in the clinic. Furthermore, the compound of the present invention exhibits particularly good duration of effect having a long half-life in vivo.

Accordingly the present invention provides a compound of the formula (II):

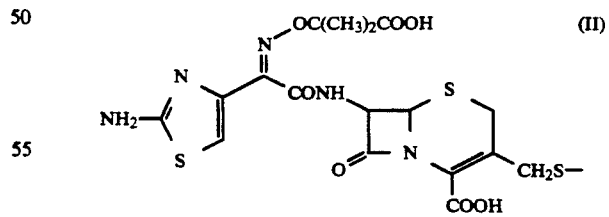

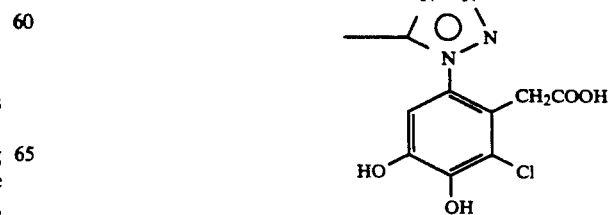

or a pharmaceutically acceptable salt or in vivo hydrolysable ester thereof.

Suitable salts include acid addition salts such as salts formed with hydrochloric, hydrobromic, citric, maleic, phosphoric and sulphuric acids. In another aspect suitable salts are base salts such as an alkali metal salt for example sodium or potassium, an alkaline earth metal salt for example calcium or magnesium, an organic amine salt for example triethylamine, morpholine, N-methylpiperidine, N-ethylpiperidine, procaine, dibenzylamine or N,N-dibenzylethylamine. A preferred salt is the sodium salt.

In vivo hydrolysable esters may be formed at the carboxy groups (—COOH) and/or hydroxy groups (—OH).

In vivo hydrolysable esters are those pharmaceutically acceptable esters that hydrolyse in the human or animal body to produce the parent hydroxy compound. Such esters can be identified by administering, e.g. intravenously to a test animal, the compound under test and subsequently examining the test animal's body fluids. Suitable in vivo hydrolysable esters include $C_{1-6}$ alkanoyloxy for example acetoxy, propionyloxy, pivaloyloxy, $C_{1-4}$ alkoxycarbonyloxy for example ethoxycarbonyloxy, phenylacetoxy and phthalidyl.

It is preferred that the compound of this invention has di-hydroxy groups and is in the form of the free acid or salt thereof.

The present invention covers all tautomeric forms of the compounds of this invention and the compounds are generally named in accordance with the 'cephem' nomenclature and numbering system proposed in J.A.C.S. 1962, 84, 3400.

In order to use a compound of the present invention or a pharmaceutically acceptable salt or in vivo hydrolysable ester thereof for the therapeutic treatment of mammals including humans, in particular in treating infection, it is normally formulated in accordance with standard pharmaceutical practice as a pharmaceutical composition.

Therefore in another aspect the present invention provides a pharmaceutical composition which comprises a compound of the formula (II) or a pharmaceutically acceptable salt or in vivo hydrolysable ester thereof and a pharmaceutically acceptable carrier.

The pharmaceutical compositions of this invention may be administered in standard manner for the disease condition that it is desired to treat, for example by oral, rectal or parenteral administration. For these purposes it may be formulated by means known to the art into the form of, for example, tablets, capsules, aqueous or oily solutions or suspensions, emulsions, dispersible powders, suppositories and sterile injectable aqueous or oily solutions or suspensions.

In addition to the pharmaceutically acceptable cephalosporin derivative of the present invention the pharmaceutical composition of the invention may also contain, or be co-administered with, one or more known drugs selected from other clinically useful antibacterial agents (for example other beta-lactams or aminoglycosides), renal tubular blocking agents (e.g. probenicid) and inhibitors of metabolising enzymes (for example inhibitors of peptidases, for example Z-2-acylamino-3-substituted propenoates).

A particular pharmaceutical composition of this invention is one suitable for oral administration in unit dosage form, for example a tablet or capsule which contains between 100 mg. and 1 g. of the compound of the formula (II) or pharmaceutically acceptable salt or in vivo hydrolysable ester thereof.

A preferred pharmaceutical composition of this invention is one suitable for intravenous, subcutaneous or intramuscular injection, for example a sterile injectable containing between 1 and 50% w/w of the compound of the formula (II) or pharmaceutically acceptable salt or in vivo hydrolysable ester thereof.

The pharmaceutical compositions of the invention will normally be administered to man in order to combat infections caused by bacteria, in the same general manner as that employed for cephalothin, cefoxitin, cephradine, ceftazidime and other known clinically used cephalosporin derivatives, due allowance being made in terms of dose levels for the potency of the cephalosporin derivative of the present invention relative to the known clinically used cephalosporins. Thus each patient will receive a daily intravenous, subcutaneous or intramuscular dose of 0.05 to 10 g., and preferably 0.1 to 5 g., of the cephalosporin derivative, the composition being administered 1 to 4 times per day, preferably 1 or 2 times a day. The intravenous, subcutaneous and intramuscular dose may be given by means of a bolus injection. Alternatively the intravenous dose may be given by continuous infusion over a period of time. Alternatively each patient will receive a daily oral dose which is approximately equivalent to the daily parenteral dose. Thus a preferred daily oral dose is 0.5 to 5 g. of the cephalosporin derivative, the composition being administered 1 to 4 times per day.

In a further aspect the present invention provides a process for preparing a compound of the formula (II) or pharmaceutically acceptable salt or in vivo hydrolysable ester thereof, which process comprises:

(a) reacting a compound of the formula (III) with a compound of the formula (IV):

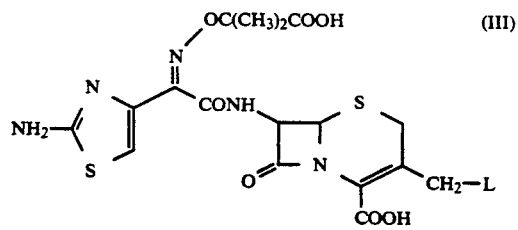

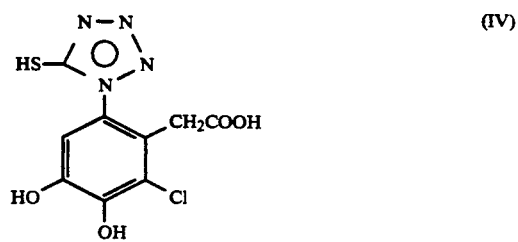

wherein L is a leaving group; or b) reacting a compound of the formula (V) with a compound of the formula (VI) or reactive derivative thereof:

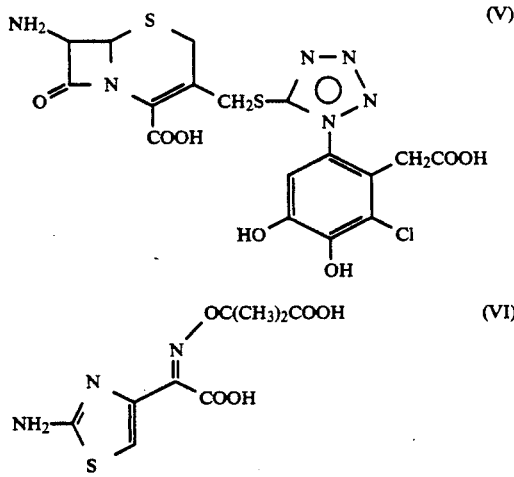

(V)

(VI)

or c) reacting a compound of the formula (VII) with a compound of the formula (VIII):

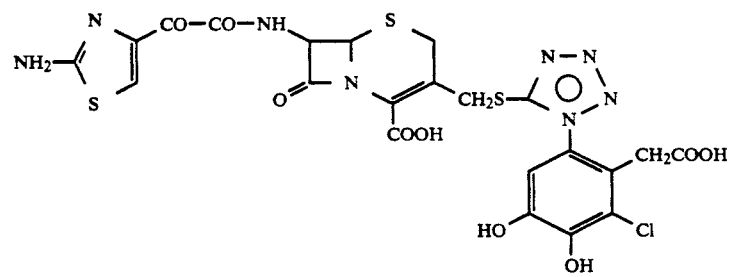

(VII)

(VIII)

or d) reacting a compound of the formula (IX) with a compound of the formula (X):

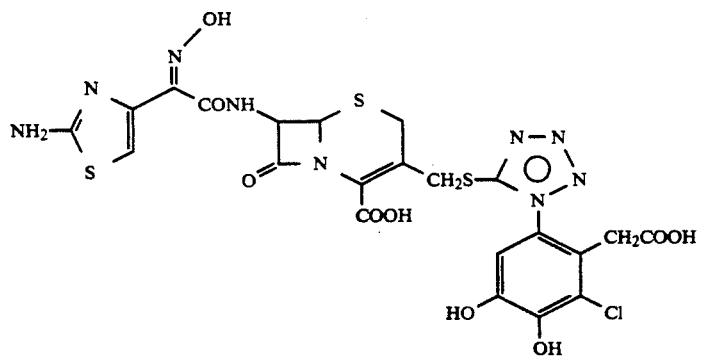

(IX)

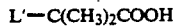

(X)

wherein L' is a leaving group: wherein any functional groups are optionally protected and thereafter, if necessary:
  i) removing any protecting group,
  ii) for preparing in vivo hydrolysable esters, esterifying corresponding carboxy and/or hydroxy groups,
  iii) forming a pharmaceutically acceptable salt.

In the reaction between compounds of the formulae (III) and (IV), conveniently L is a leaving group such as halo for example iodo, bromo or chloro, or is $C_{1-4}$ alkanoyloxy for example acetoxy. The cephalosporin starting materials of the formula (III) are known in the art or are made by methods analogous thereto; see for example EP-A-127992 and EP-A-164944. The compound of the formula (IV) is readily prepared by the method known to those skilled in the art, for example by the methods disclosed in Example 1 herein.

The reaction between compounds of the formulae (V) and (VI) is performed under conditions conventional in the cephalosporin art, for example under standard acylation conditions wherein for example the acid is activated as an acid bromide, acid chloride, or activated ester, or the reaction is performed in the presence of a coupling reagent such as dicyclohexylcarbodiimide. The carboxy group of the 1-carboxy-1-methylethoxyimine may be optionally protected during the acylation reaction.

The compounds of the formula (V) can be prepared in a manner analogous to that described for the compounds of the formula (II) with the 7-amino group being optionally protected.

The reaction between compounds of the formula (VII) and $NH_2OC(CH_3)_2COOH$ is performed under conditions standard in the general chemical and/or cephalosporin art. The compounds of the formula (VII) can be prepared in a manner analogous to that described for the compounds of the formula (II).

The reaction between the compound of the formula (IX) and a compound of the formula $L'C(CH_3)_2COOH$ is performed under conditions standard in the general chemical and/or cephalosporin art.

The compounds of the formulae (V), (VII) and (IX) are novel and as such form further aspects of the present invention.

In the process of this invention may functional group can be optionally protected, if appropriate. Such protecting groups may in general be chosen from any of the groups described in the literature or known to the skilled chemist as appropriate for the protection of the group in question, and may be introduced by conventional methods.

Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the sake of convenience, in which "lower" signifies that the group to which it is applied preferably has 1-4 carbon atoms. It will be understood that these examples are not exhaustive. Where specific examples of methods for the removal of protecting groups are given below these are similarly not exhaustive. The use of protecting groups and methods of deprotection not specifically mentioned is of course within the scope of the invention.

A carboxyl protecting group may be the residue of an ester-forming aliphatic or araliphatic alcohol or of an ester-forming phenol, silanol or stannanol (the said alcohol, phenol, silanol or stannanol preferably containing 1-20 carbon atoms).

Examples of carboxyl protecting groups include straight or branched chain (1-12 C)alkyl groups (e.g. isopropyl, t-butyl); halo lower alkyl groups (e.g. 2-iodoethyl, 2,2,2-trichloroethyl); lower alkoxy lower alkyl groups (e.g. methoxymethyl, ethoxymethyl, isobutoxymethyl); lower aliphatic acyloxy lower alkyl groups, (e.g. acetoxymethyl, propionyloxymethyl, butyryloxymethyl, pivaloyloxymethyl); lower alkoxycarbonyloxy lower alkyl groups (e.g. 1-methoxy-carbonyloxyethyl, 1-ethoxycarbonyloxyethyl); aryl lower alkyl groups (e.g. p-methoxybenzyl, o-nitrobenzyl, p-nitrobenzyl, benzhydryl and phthalidyl); tri(lower alkyl)silyl groups (e.g. trimethylsilyl and t-butyldimethylsilyl); tri(lower alkyl)silyl lower alkyl groups (e.g. trimethylsilylethyl); and (2-6 C)alkenyl groups (e.g. allyl and vinylethyl).

Methods particularly appropriate for the removal of carboxyl protecting groups include for example acid-, base-, metal- or enzymically-catalysed hydrolysis.

Examples of hydroxyl protecting groups include lower alkanoyl groups (e.g. acetyl); lower alkoxycarbonyl groups (e.g. t-butoxycarbonyl); halo lower alkoxycarbonyl groups (e.g. 2-iodoethoxycarbonyl, 2,2,2-trichloroethoxycarbonyl); aryl lower alkoxycarbonyl groups (e.g. benzoyloxycarbonyl, p-methoxybenzyloxycarbonyl, o-nitrobenzyloxycarbonyl, p-nitrobenzyloxycarbonyl); tri lower alkylsilyl (e.g. trimethylsilyl, t-butyldimethysilyl) and aryl lower alkyl (e.g. benzyl) groups. In addition two hydroxy groups substituted on adjacent carbon atoms, for example in the catechol moiety, may be protected in the form of a cyclic acetal such as the methylenedioxy moiety.

Examples of amino protecting groups include formyl, aralkyl groups (e.g. benzyl and substituted benzyl, e.g. p-methoxybenzyl, nitrobenzyl and 2,4-dimethoxybenzyl, and triphenylmethyl); di-p-anisylmethyl and furylmethyl groups; acyl (e.g. alkoxycarbonyl and aralkoxycarbonyl e.g. t-butoxycarbonyl and benzyloxycarbonyl); trialkylsilyl (e.g. trimethylsilyl and t-butyldimethylsilyl); alkylidene (e.g. methylidene); benzylidene and substituted benzylidene groups; and the phthalimido groups.

Esterification of hydroxy groups to form in vivo hydrolysable esters is performed in conventional manner.

The following biological test methods, data and Examples serve to illustrate this invention.

ANTIBACTERIAL ACTIVITY

The pharmaceutically acceptable cephalosporin compounds of the present invention are useful antibacterial agents having a broad spectrum of activity in vitro against standard laboratory microorganisms, both Gram-negative and Gram-positive, which are used to screen for activity against pathogenic bacteria. The antibacterial spectrum and potency of a particular compound may be determined in a standard test system. The compounds have particularly high activity in vitro against strains of Pseudomonas aeruginosa.

The antibacterial properties of the compounds of the invention may also be demonstrated in vivo in conventional acute lethal challenge tests in mice.

Cephalosporin derivatives have generally been found to be relatively non-toxic to warm-blooded animals, and this generalisation holds true for the compounds of the present invention. Compounds representative of the present invention were administered to mice at doses in excess of those required to afford protection against bacterial infections, and no overt toxic symptoms or side effects attributable to the administered compounds were noted.

The following results were obtained for Example 1 and two comparative compounds on a standard in vitro test system using Diagnostic Sensitivity Test agar medium. The antibacterial activity is described in terms of the minimum inhibitory concentration (MIC) determined by the agar-dilution technique with an inoculum size of $10^4$ CFU/spot.

Compound (A) is a representative compound, Example 9, from EP-A-272827 and compound (B) is ceftazidime.

The compound of Example 1 exhibits particularly good duration of effect, as evidenced in studies in marmosets. The half-life (t $\frac{1}{2}$) is substantially and significantly longer than that of representative compounds of EP-A-272827.

|  | Compound of Example 1 | Compound (A) |
|---|---|---|
| t$\frac{1}{2}$ (hours) | 20.7 | 4.5 | when dosed to marmosets at 3 mg/kg.

This means that comparatively lower doses of the compound of Example 1 may be administered to patients in need thereof or that substantially higher and longer antibiotic cover may be achieved.

| | MIC (μg/ml) | | |
|---|---|---|---|
| ORGANISM | Compound of Ex 1 | Compound (A) | Compound (B) |
| P. aeruginosa 18S(A8101024) | 0.004 | 0.008 | 2 |
| P. aeruginosa DR18SH(A81011020) | 0.016 | 0.06 | 16 |
| P. aeruginosa PU21(A8101028) | 0.008 | 0.008 | 1 |
| Ent. cloacae P99−(A8401054) | 0.125 | 0.25 | 0.125 |
| Ent. cloacae P99+(A8401053) | 1 | 1 | 32 |

-continued

| ORGANISM | MIC (µg/ml) | | |
|---|---|---|---|
| | Compound of Ex 1 | Compound (A) | Compound (B) |
| Ent. cloacae DR(A8401108) | 0.25 | 4 | 32 |
| Ent. cloacae DR(A8401109) | 0.125 | 2 | 32 |
| Serr. marcesens (A8421003) | 0.008 | 0.03 | 0.25 |
| Serr. marcesens DR(A8421078) | 0.008 | 0.03 | 0.5 |
| Pr. morganii (A8433001) | 0.008 | 0.25 | 0.06 |
| Pr. morganii DR(A8433062) | 0.06 | 4 | 16 |
| E. coli DCO(A8341098) | 0.002 | 0.008 | 0.125 |
| E. coli JS3 RTEM(A8341135) | 0.001 | 0.008 | 0.06 |
| Citro. freundii DR(A8382031) | 0.25 | 1 | 128 |
| Citro. freundii DR(A8382034) | 0.5 | 2 | 64 |
| A. anitratus (A8322001) | 0.06 | 0.125 | 16 |
| P. stuartii DR(A8382031) | 0.03 | 4 | 4 |
| K. oxytoca D1+(A8395056) | 0.004 | 0.016 | 0.5 |
| S. dublin (A8369001) | 0.004 | 0.008 | 0.125 |
| Strep. pyogenes (A8681018) | 0.5 | 0.25 | 0.125 |
| Strep. pneumoniae (A8671001) | 0.03 | 0.03 | 0.125 |

EXAMPLE 1

7-[2-(2-Aminothiazol-4-yl)-2-((Z)-1-carboxy-1-methylethoxyimino)acetamido]-3-[(1-(2-carboxymethyl-3-chloro-4,5-dihydroxyphenyl)tetrazol-5-yl)thiomethyl]-ceph-3-em-4-carboxylic acid 7-[2-(2-Aminothiazol-4-yl)-2-((Z)-1-t-butoxycarboxy-1-methyl ethoxyimino)acetamido]-3-[(1-(2-carboxymethyl-3-chloro-4,5-dihydroxyphenyl)-tetrazol-5-yl)thiomethyl]ceph-3-em-4-carboxylic acid (0.875 g) was treated with trifluoroacetic acid (10 ml) at room temperature for 1 hour. The mixture was evaporated and the residue triturated with ether to give a solid which was collected by filtration and purified by HPLC (AMICON $C_{18}$ 15 µm), eluting with methanol/water/acetic acid (35:65:1 to 40:60:1) [Dimethylformamide was necessary for dissolution of the crude product.] Thus was obtained the title product (0.38 g); NMR (DMSO-$d_6$/CD$_3$CO$_2$D/CF$_3$CO$_2$D) 1.55(s,6H, —C(CH$_3$)$_2$—); 3.35(s,2H,—CH$_2$COOH); 3.60 and 3.85(2d, J=18 Hz, —SCH$_2$—); 4.30 and 4.65 (2d,J=11.5 Hz, 2H, —CH$_2$—S—tetrazole); 5.20 and 5.85(2d, J=4.5 Hz, 2H, $\overline{H_6}$ and H$_7$); 6.85 (s,1H, aromatic); 7.05(s,1H, thiazole).

The above acid, together with material from another experiment, (32.1 g) was suspended in distilled water (450 ml). The pH was taken to 5 with aqueous sodium bicarbonate, the solution was filtered and lyophilised to give the sodium salt (34.3 g); NMR (as above); IR 1760cm$^{-1}$.

The starting material was prepared as follows:

a) 3,4-Dimethoxyphenylacetic acid (7.84 g) was solubilised in ether (100 ml) and acetic acid (20 ml). Fuming nitric acid (1.68 ml) was added dropwise to the solution. Stirring was maintained at room temperature for 16 hours. The precipitate was collected by filtration, washed with ether and dried to give 4,5-dimethoxy-2-nitrophenylacetic acid (4.19 g); NMR (DMSO-$d_6$) 3.88(s,3H); 3.80(s,3H); 3.97(s,2H); 7.15(s,1H); 7.70(s,1H).

b) The product from a) above (together with material from another experiment) (48.2 g) was suspended in water (500 ml). Potassium hydroxide (78 g) was added slowly and the resultant solution heated at reflux for 10 hours. The solution was cooled and adjusted to pH 1 with concentrated hydrochloric acid. The resultant crystalline solid was collected by filtration, washed with cold water and dried to give 5-hydroxy-4-methoxy-2-nitrophenylacetic acid (42 g); NMR (DMSO-$d_6$/CD$_3$COOD/CF$_3$COOD) 3.87(s,5H); 6.86(s,1H); 7.7(s,1H).

c) Part of the product from b) (20 g) was dissolved in acetic acid (100 ml) at 40° C. A stream of chlorine was passed through the solution and a crystalline solid formed after 30 minutes. Nitrogen gas was passed through the mixture which was cooled to 15° C. and the crystalline solid was collected by filtration, washed with acetic acid and dried to give 2-chloro-3-hydroxy-4-methoxy-6-nitrophenylacetic acid (17.3 g); m.p. 231° C.; NMR (DMSO-$d_6$/CD$_3$COOD/CF$_3$COOD) 3.9(s,3H); 4.02(s,2H); 4.67(s,1H).

d) The product from c) (17.2 g) in dimethylformamide (400 ml) was treated with iodomethane (20 ml) and potassium carbonate (19 g). The reaction mixture was heated for 4 hours at 50° C. and evaporated. The residue was taken up in water and extracted into ethyl acetate to give, as a reddish oil, methyl 2-chloro-3,4-dimethoxy-6-nitrophenyl acetate (19 g); NMR(DMSO-$d_6$/CF$_3$COOD) 3.63(s,3H); 3.88(s,3H); 3.93(s,3H); 4.05(s,2H); 7.74(s,1H).

e) To a solution of the product from d) (19 g) in methanol (250 ml) was added potassium hydroxide (5 g) in water (250 ml). The resultant mixture was heated at reflux for 2 hours to give a solution. This was cooled and methanol was removed by evaporation. The aqueous layer was washed with ethyl acetate and acidified with 6N hydrochloric acid to give an orange solid which was collected by filtration, washed with water and dried to give 2-chloro-3,4-dimethoxy-6-nitrophenyl acetic acid (16.5 g); NMR(DMSO-$d_6$/CF$_3$COOD) 3.86(s,3H); 3.93(s,3H); 3.96(s,2H); 7.72(s,1H).

f) Part of the product from e) above (10 g) in methanol (100 ml) was hydrogenated (1.25 bar) over 10% palladium on carbon (100 mg) for 1 hour. The mixture was filtered through diatomaceous earth and the filtrate evaporated to give a residue. This residue was triturated with dichloromethane and the resultant solid collected by filtration, washed with dichloromethane and dried to give 6-amino-2-chloro-3,4-dimethoxyphenylacetic acid (7.25 g); NMR (DMSO-$d_6$) 3.52(s,2H); 3.6(s,3H); 3.72(s,3H); 6.4(s,1H).

g) The product from f) (7.35 g) was dissolved in a mixture of water (100 ml) and acetonitrile (100 ml) and cooled to ice-bath temperature. Thiophosgene (2.65 ml) was added dropwise and the temperature then allowed to rise to ambient. Crystals formed; after 1 hour acetonitrile was removed by evaporation and the beige solid collected by filtration, washed and dried to give 2-carboxymethyl-3-chloro-4,5-dimethoxyphenylisothiocyanate (8.2 g); NMR (DMSO-$d_6$) 3.75(s,2H); 3.77(s,3H); 3.87(s,3H); 7.23(s,1H).

h) To a suspension of the isothiocyanate from g) (7.5 g) in water (200 ml) was added sodium bicarbonate (3.375 g) and sodium azide (2.625 g). The reaction mixture was heated at 80° C. for 30 minutes, cooled, filtered, washed with ethyl acetate and acidified with 6N hydrochloric acid. The resultant beige solid was collected by filtration, washed and dried to give 1-(2-carboxymethyl-3-chloro-4,5-dimethoxyphenyl)-2-mercaptotetrazole (7 g); NMR (DMSO-$d_6$/CF$_3$COOD) 3.57(s,2H); 3.85(s,6H); 7.34(s,1H).

i) To the product from h) (6.0 g) in suspension in dichloromethane (450 ml) was added bis trimethylsilylacetamide (9 ml) to give a solution which was cooled to −20° C. Boron tribromide (8.6 ml) was added dropwise and the temperature allowed to rise to ambient. The reaction mixture was stirred for 1 hour, evaporated, hydrolysed with crushed ice and purified by column chromatography on HP20SS resin, eluting with methanol/water/acetic acid (40:60:1), to give 1-(2-carboxymethyl-3-chloro-4,5-dihydroxyphenyl)-2-mercaptotetrazole (4.5 g); NMR DMSO-d$_6$/CD$_3$COOD/CF$_3$COOD) 3.48(s,2H); 6.93(s,1H).

j) To a solution of product i) (2.3 g) in dimethylformamide (10 ml) was added triethylamine (1.15 ml) and 7-amino-3-iodomethyl-ceph-3-em-4-carboxylic r17d (2.67 g). The reaction mixture was stirred for 2 hours at ambient temperature. 2-Aminothiazol-4-yl-2-((Z)-1-t-butoxycarbonyl-1-methylethoxyimino)acetyl 2-benzthiazolyl thioester (2.5 g) and triethylamine (0.75 ml) were added and the resultant mixture stirred for 2 hours at ambient temperature. Dimethylformamide was removed by evaporation and the residue triturated with ether to give a solid which was dissolved in a little dimethylformamide and purified by column chromatography on HP20SS resin, eluting with methanol/water/acetic acid (65:35:1), to give 7-[2-(2-aminothiazol-4--yl)-2-((Z)-1-t-butoxycarbonyl-1-methylethoxyimino)acetamido]-3-[(1-(2-carboxymethyl-3-chloro-4,5-dihydroxyphenyl)tetrazol-5-yl)thiomethyl]ceph-3-em-4-carboxylic acid (0.905 g); NMR (DMSO-d$_6$/CF$_3$COOD/CF$_3$COOD) 1.55(s,6H); 3.35(s,2H); 3.60(d,1H); 3.85(d,1H); 4.30(d,1H); 4.65(d,1H); 5.20(d,1H); 5.85(d,1H); 6.85(s,1H); 7.05(s,1H).

The starting material for Example 1 was prepared in an alternative manner as follows:

i) To 2-chloro-3-hydroxy-4-methoxy-6-nitrophenylacetic acid (52 g) in methanol (600 ml) was added triethylamine (56 ml) and 10% palladium on carbon (4 g). The mixture was hydrogenated for 3 hours at 1.4 bar, filtered, evaporated and the residue crystallised to give the triethylamine salt of 2-chloro-3-hydroxy-4-methoxy-6-aminophenylacetic acid (64 g); NMR (DMSO-d$_6$/CD$_3$COD/CF$_3$COOD) 1.17(t,9H); 3.05(s,6H); 3.54(s,2H); 3.73(s,3H); 6.4(s,1H).

ii) To a solution of the product from i) (33 g) in a mixture of water (150 ml) and acetonitrile (50 ml), at 0° C., was added dropwise thiophosgene (8.5 ml). The solution was stirred at 0° C. for 30 minutes and at ambient temperature for a further 30 minutes. Water (100 ml) was added and the isothiocyanate was collected by filtration. This precipitate was suspended in water (150 ml), sodium azide (9.7 g) was added and the pH adjusted to 8.5 with 2N sodium bicarbonate. The resultant solution was heated at 60° C. for 45 minutes whilst maintaining the pH at 8.5 by the addition of 2N sodium hydroxide. The solution was cooled and acidified to pH2 with concentrated HCl. The precipitate was collected by filtration and dried to give 1-(2-carboxymethyl-3-chloro-4-hydroxy-5-methoxyphenyl)-2-mercaptotetrazole (23.5 g); NMR (DMSO-d$_6$/CF$_3$COOD) 3.85(s,3H); 7.20(s,1H).

iii) To the product from ii) (100 g) suspended in dichloromethane (1 l) was added bistrimethylsilylacetamide (240 ml), with stirring, to give a solution. This was cooled to −50° C., boron tribromide (170 ml) was added dropwise and the temperature allowed to rise to ambient. The reaction mixture was evaporated, hydrolysed with crushed ice and purified by column chromatography on HP20SS resin, eluting with methanol/water/acetic acid (30:70:1) to give 1-(2-carboxymethyl-3-chloro-4,5-dihydroxyphenyl)-2-mercaptotetrazole (73 g).

iv) 7-Amino-3-acetoxymethylceph-3-em-4-carboxylic acid (10 g) and the product from iii) (11.2 g) in acetonitrile (350 ml) were rapidly stirred with boron trifluoride etherate (60 ml). The mixture, at 40° C., was stirred for 1 hour under argon. The solvents were removed by evaporation and the residue was purified by column chromatography on HP20SS resin, eluting with methanol/water/acetic acid (0:100:1 to 35:65:1) to give 7-amino-3-[(1-(2-carboxymethyl-3-chloro-4,5-dihydroxyphenyl)tetrazol-5-yl)thiomethyl]ceph-3-em-4-carboxylic acid (10.9 g); NMR(DMSO-d$_6$/CF$_3$COOD) 3.35(s,2H); 3.80(broad s,2H); 4.30 and 4.65(2 d,2H); 5.15(s,2H); 6.90(s,1H).

v) This was reacted with 2-aminothiazol-4-yl-2-((Z)-1-t-butoxycarbonyl-1-methylethoxyimino)acetyl-2-benzthiazolyl thioester and triethylamine in a manner as described in j) above.

We claim:

1. A compound of the formula (II):

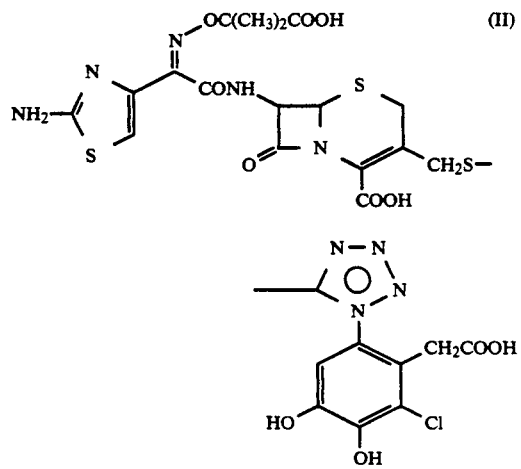

or a pharmaceutically acceptable salt or in vivo hydrolysable ester thereof.

2. A compound according to claim 1 in the form of a sodium salt.

3. 7-[2-(2-Aminothiazol-4-yl)-2-((Z)-1-carboxy-1-methylethoxyimino)acetamido]-3-[(1-(2-carboxymethyl-3-chloro-4,5-dihydroxyphenyl)tetrazol-5-yl)thiomethyl]ceph-3-em-4-carboxylic acid.

4. An antibacterial pharmaceutical composition which comprises a compound according to claim 1 and a pharmaceutically acceptable carrier.

5. A composition according to claim 4 in the form of an intravenous, sterile injection.

6. A composition according to claim 4 in the form of an intramuscular, sterile injection.

7. A method of antibacterial treatment which comprises administering to a patient in need thereof an antibacterially effective amount of a compound according to claim 1.

8. The compound 7-[2-(2-aminothiazol-4-yl)-2-((Z)-1-carboxy-1-methylethoxyimino)acetamido]-3-[(1-(2-carboxy-methyl-3-chloro-4,5-dihydroxyphenyl)-tetrazol-5-yl)thiomethyl]ceph-3-em-4-carboxylate sodium salt.

* * * * *